United States Patent [19]

VandenBerg

[11] Patent Number: Plant 7,513

[45] Date of Patent: Apr. 30, 1991

[54] CHRYSANTHEMUM PLANT NAMED NAOMI

[75] Inventor: Cornelis P. VandenBerg, Salinas, Calif.

[73] Assignee: Yoder Brothers, Inc., Barberton, Ohio

[21] Appl. No.: 458,837

[22] Filed: Dec. 29, 1989

[51] Int. Cl.[5] ..... A01H 5/00

[52] U.S. Cl. ..... Plt./74

[58] Field of Search ..... Plt./74

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Naomi particularly characterized by its flat capitulum form; spooned daisy capitulum type; purple ray floret color; diameter across face of capitulum of 63 to 70 mm when fully opened; medium to tall plant height with semi-spreading and prolific branching pattern; average natural season flowering date of August 29 in Salinas, Calif. and September 23 in Hightstown, N.J.; uniform seven week photoperiodic flowering response to short days in photoperiodic controlled flowering programs; and durable, uniform performance.

3 Drawing Sheets

The present invention comprises a new and distinct cultivar of Chrysanthemum, botanically known as *Dendranthema grandiflora*, and referred to by the cultivar name Naomi.

Naomi, identified as 85-042002, was originated by the inventor Cornelis P. VandenBerg from a cross made in a controlled breeding program in Salinas, Calif., in 1985.

The female parent and the male parent of Naomi were both unnamed seedlings, identified as 82-N14003 and 82-M29001, respectively. The female parent was a pink decorative, and the male parent was a pink spooned daisy.

Naomi was discovered and selected as one flowering plant within the progeny of the stated cross by Cornelis P. VandenBerg in January 1986, in a controlled environment in Salinas, Calif.

The first act of asexual reproduction of Naomi was accomplished when vegetative cuttings were taken from the initial selection in April 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Naomi are firmly fixed and are retained through successive generations of asexual reproduction.

Naomi has not been observed under all possible environmental conditions. The phenotype may vary significantly with variations in environment such as temperature, light intensity and daylength.

The following observations, measurements and comparisons describe plants grown in controlled open areas in Salinas, Calif. and in Hightstown, N.J., and photoperiodic controlled programs conducted in Salinas, Calif. Rooted cuttings were established in soil and maintained outdoors under the natural temperature and daylength prevailing during June through October. Single pinching was practiced with all branches and buds retained.

The following traits have been repeatedly observed and are determined to be basic characteristics of Naomi, which, in combination, distinguish this Chrysanthemum as a new and distinct cultivar:

1. Flat capitulum form.

2. Spooned daisy capitulum type.
3. Purple ray floret color.
4. Diameter across face of capitulum of 63–70 mm when fully opened.
5. Medium to tall plant height averaging 38 cm from soil line at time of flowering based on June 15 planting in Hightstown, N.J.
6. Spreading and prolific branching pattern, averaging 7 branches per plant after pinch two weeks after planting a rooted cutting in Hightstown, N.J.
7. Average natural season flowering date of August 29 in Salinas, Calif., and September 23 in Hightstown, N.J., based on several years of trial flowering.
8. Uniform seven week photoperiodic flowering response to short days in photoperiodic controlled flowering programs.
9. Durable, uniform performance.

The accompanying photographic drawings show typical inflorescence and leaf characteristics of Naomi, with the colors being as nearly true as possible with illustrations of this type.

Sheet 1 is a color photograph of Naomi grown as a pinched spray pot mum in a 15 cm pot.

Sheet 2 is a black and white photograph of three views of the inflorescence of Naomi.

Sheet 3 is a black and white photograph showing the upper and under sides of the leaves of Naomi at three stages of development (mature, intermediate and immature).

Of the commercial garden mum cultivars known to the inventor, the most similar in comparison to Naomi is the cultivar identified as Lancer, a flat spooned daisy, dark lavender in color, and disclosed in U.S. Plant Pat. No. 4,531. Reference is made to attached Chart A which compares certain characteristics of Naomi to the same characteristics of Lancer.

Similar traits are capitulum form and type, and natural and controlled response periods. Naomi has a brighter ray floret color than Lancer. Naomi also has a more true daisy form, with Lander having a higher number of ray florets per flower, being almost semi-double. Even though both Naomi and Lancer can be generally described as having a semi-spreading branching pattern, Naomi has more branches per plant after pinch than Lancer and a more spreading branching pattern. Naomi also has a smaller diameter of capitulum.

In the following description color references are made to The Royal Horticultural Society Colour Chart. The color values were determined on plant material grown in a controlled greenhouse environment in Salinas, Calif. on Sep. 19, 1989.

Classification:

*Botanical.*—*Dendranthema grandiflora* cv Naomi.

*Commercial.*—Flat spooned daisy spray pot mum and garden mum.

INFLORESCENCE

A. Capitulum:

*Form.*—Flat.

*Type.*—Spooned daisy.

*Diameter across face.*—63–70 mm when fully opened.

B. Corolla of ray florets:

*Color (general tonality from a distance of three meters).*—Purple.

*Color (upper surface).*—(Spoon tips) 78B fading to 78C.

*Color (under surface).*—(Tubes) Base 75D. Apical portion of underside 75D, streaked and tinged with 78C.

*Shape.*—Longitudinal slightly incurved, spooned tip.

C. Corolla of disc florets:

*Color (mature).*—Closest to 14B.

*Color (immature).*—Yellow, tinged with 144B.

D. Reproductive organs:

*Androecium.*—Present on disc florets only; moderate pollen.

*Gynoecium.*—Present on both ray and disc florets.

PLANT

A. General appearance:

*Height.*—Medium to tall.

*Branching pattern.*—Semi-spreading and prolific.

B. Foliage:

*Color (upper surface).*—147A.

*Color (under surface).*—147B.

*Shape.*—See photograph.

CHART A

COMPARISON OF NAOMI AND LANCER

| CHARACTERISTIC | NAOMI | LANCER |
|---|---|---|
| Ray Floret Color | Purple | Dark lavender-pink |
| Capitulum Form and Type | Flat spooned daisy | Flat spooned daisy |
| Branching Pattern | Semi-spreading and prolific | Semi-spreading |
| Diameter Across Face of Capitulum | 63–70 mm | 83–100 mm |
| Controlled Response | 7 weeks | 7 weeks |
| Average Natural Season Flower date: | | |
| In Salinas, California: | August 29 | August 28 |
| In Hightstown, New Jersey: | September 23 | September 22 |

Comparisons Made of Plants Grown Under Natural Season Outdoor Conditions In Salinas, California and in Hightstown, New Jersey

I claim:

1. A new and distinct Chrysanthemum plant named Naomi, as described and illustrated.

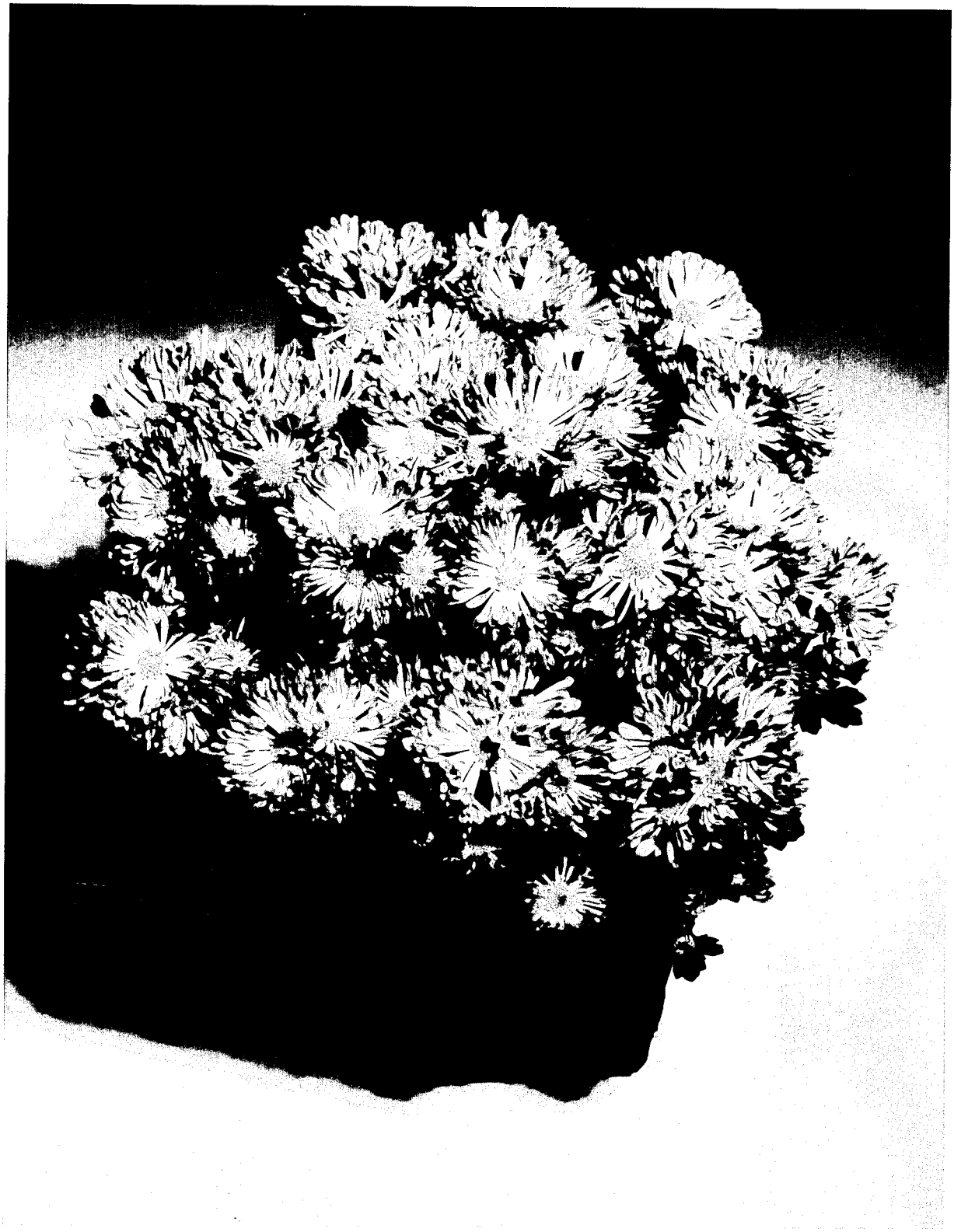

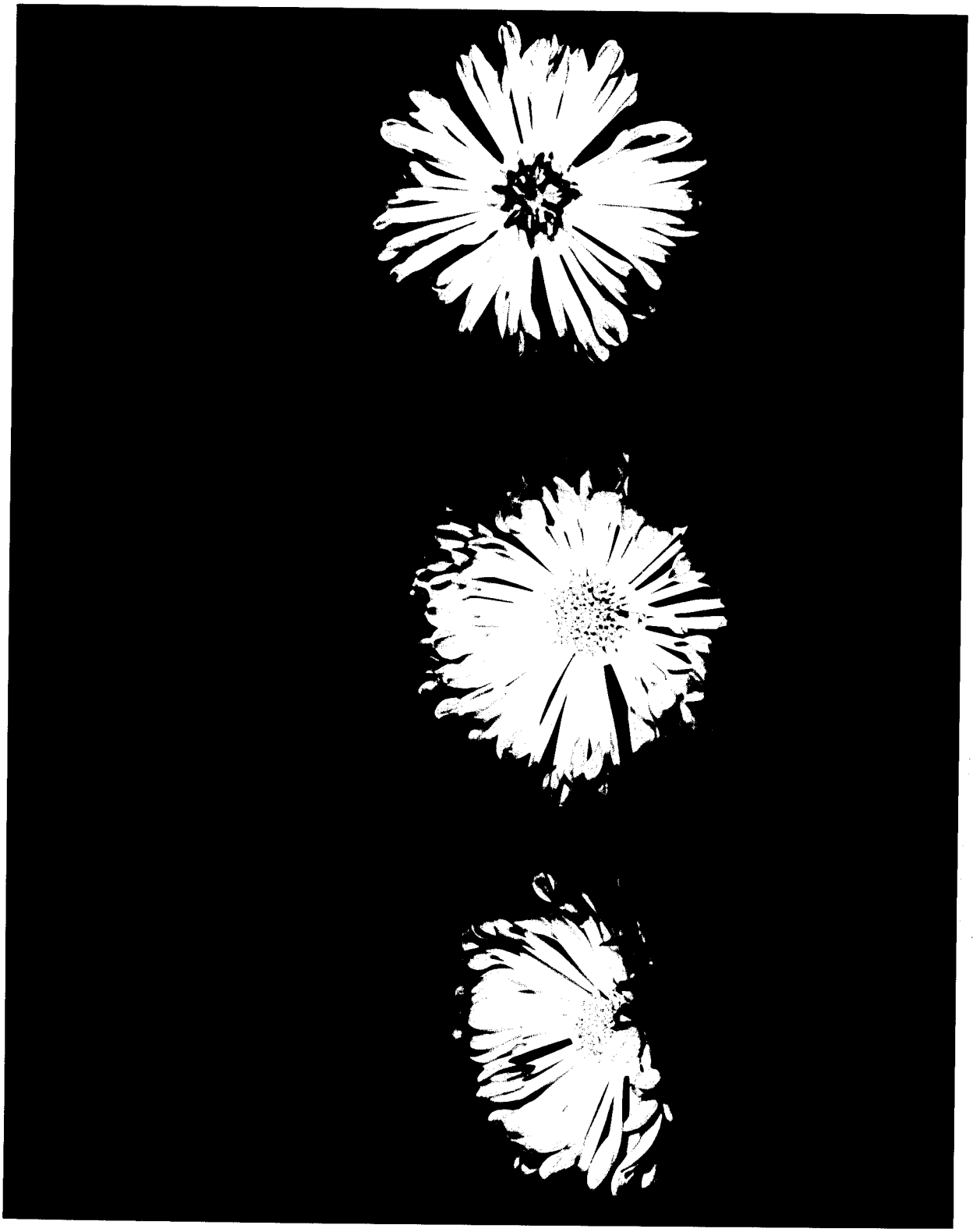

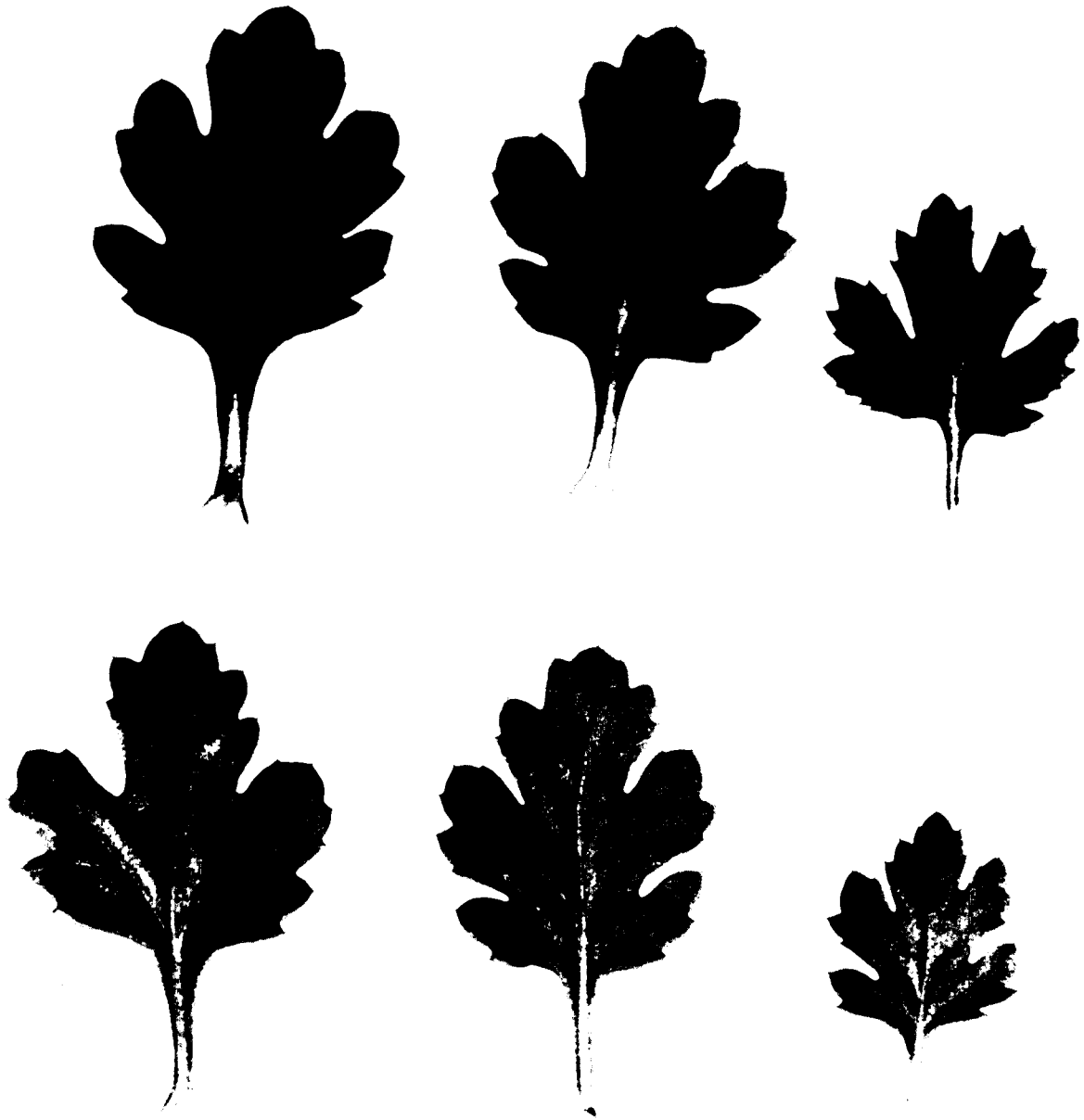

* * * * *